US006936034B2

United States Patent
Watkins

(10) Patent No.: US 6,936,034 B2
(45) Date of Patent: Aug. 30, 2005

(54) INSULIN SYRINGE WITH MAGNIFIED SHEATH

(75) Inventor: Tasheem Watkins, 39 Naylor Ave., Clementon, NJ (US) 08021

(73) Assignee: Tasheem Watkins, Clementon, NJ (US)

( * ) Notice: Subject to any disclaimer, the term of this patent is extended or adjusted under 35 U.S.C. 154(b) by 47 days.

(21) Appl. No.: 10/721,325

(22) Filed: Nov. 26, 2003

(65) Prior Publication Data

US 2005/0113764 A1 May 26, 2005

(51) Int. Cl.[7] .......................... A61M 5/32; A61M 5/00; G02B 27/02
(52) U.S. Cl. ...................... 604/197; 604/187; 604/198; 359/441; 359/442
(58) Field of Search ................ 604/181–182, 604/187–189, 192, 197, 198; 359/440–442, 359/436, 809; 374/100, 158, 191; 128/919

(56) References Cited

U.S. PATENT DOCUMENTS

| 2,586,581 | A | | 2/1952 | Tschischeck |
| 4,743,234 | A | | 5/1988 | Leopoldi et al. |
| 5,204,775 | A | * | 4/1993 | McDevitt ..................... 359/442 |
| 5,309,279 | A | * | 5/1994 | Halstead ..................... 359/442 |
| 5,498,243 | A | * | 3/1996 | Vallelunga et al. ......... 604/197 |
| 5,595,566 | A | | 1/1997 | Vallelunga et al. |
| 6,001,082 | A | | 12/1999 | Dair et al. |

FOREIGN PATENT DOCUMENTS

EP          0 084 583 A1       8/1983

* cited by examiner

*Primary Examiner*—Nicholas D. Lucchesi
*Assistant Examiner*—Catherine S. Williams
(74) *Attorney, Agent, or Firm*—Litman Law; Richard C. Litman

(57) ABSTRACT

The insulin syringe with magnified sheath is a syringe with a transparent outer sleeve constructed of a material capable of magnifying printed information. The outer sleeve is slidably attached to the syringe barrel and can lock into a retracted position where it surrounds the syringe barrel and magnifies the dosage indicia thereon while exposing the syringe needle for use or can lock into an extended position where it surrounds the needle to help prevent inadvertent needle sticks.

3 Claims, 4 Drawing Sheets

INSULIN SYRINGE WITH MAGNIFIED SHEATH

BACKGROUND OF THE INVENTION

1. Field of the Invention

The present invention relates to insulin syringes and more particularly to an insulin syringe with a magnified sheath that both enables a diabetic or other person whose sight is impaired to more easily read the graduated dosage numbers on the syringe barrel, and also provides a slidable shield to protect against accidental needle sticks.

2. Description of the Related Art

It is well known that diabetics must exercise great care in determining the amount of insulin to inject into their bodies. Yet, it is also known that diabetics often suffer failing eyesight which makes it difficult to adequately distinguish the graduated numbers on the side of a syringe barrel and thus to ensure a proper dosage of insulin. But given that an improper dosage of insulin can result in serious consequences, it is critical that the diabetic be able to clearly and accurately determine the amount of insulin loaded in a syringe prior to injection. While the prior art does teach some devices for improving the visibility of the graduated numbers on a syringe barrel, each of these devices has at least one drawback.

Additionally, although less serious, diabetics continually face the risk of accidental needle sticks. Diabetics must receive injections frequently and therefore are exposed to bare needles frequently. Even when cautious, a diabetic injecting himself with insulin can occasionally slip and accidentally stick himself or another person. The prior art does include syringes with safety features to minimize the risk of a needle stick but these features are generally incompatible with a means for magnifying the graduated numbers on the syringe barrel.

Worse yet, diabetics are known to experience a loss of finger dexterity due to insufficient blood flow to extremities such as the fingertips. This decreased finger dexterity complicates the use and manipulation of small objects or objects with small parts. Specifically, with reduced finger dexterity, a diabetic often experiences difficultly manipulating existing known means for magnifying dosage numbers on a syringe and for protecting against inadvertent needle sticks.

Thus, an improvement in insulin syringes that would enable a diabetic to more easily read the dosage indicia on a syringe barrel and to protect against inadvertent needle sticks while minimizing the required level of finger dexterity is needed.

U.S. Pat. No. 2,586,581 issued Feb. 19, 1952 to M. E. Tschischeck (magnifying attachment for syringes); and U.S. Pat. No. 4,743,234 issued May 10, 1988 to N. Leopoldi et al. (syringe magnifier) each teaches a magnifying device that is attached to one side of a syringe. However, because the devices do not completely encircle the syringe, each device must be manually positioned on the syringe barrel such that the magnifying portion of the device is aligned over the graduation indicia. Furthermore, neither device also serves as a means of preventing inadvertent needle sticks.

U.S. Pat. Nos. 5,498,243 and 5,595,566 issued respectively on Mar. 12, 1996 and Jan. 21, 1997 to A. J. Vallelunga et al. teach a hollow sleeve and snap ring assembly that can be attached to the housing of a syringe. The sleeve includes an elongated magnifying window running lengthwise along one of its sides. However, because the window is only on one side, the window must be manually positioned on the syringe barrel such that the magnifying portion of the device is aligned over the graduation indicia. Furthermore, the snap ring adds to the complexity of manufacturing and assembling the device.

U.S. Pat. No. 6,001,082 issued Dec. 14, 1999 to T. M. Dair et al. teaches a medication delivery pen with a magnifier integrated in the pocket clip. When the magnifier is positioned over a selected dosage setting by rotating the clip about the axis of the pen, the pen dispenses the selected dosage of insulin from a removable capsule. However, although useful when attached to a medication delivery pen, the clip is not suited for use with a conventional syringe.

European Pat. App. No. 0084583 published Aug. 3, 1983 on behalf of inventors H. Brown et al. teaches a magnification guide for loading a syringe. The guide consists of an elongated transparent magnifying member that has a recessed area along one side that is used to align the top of a medical vial with the needle of a syringe. The most obvious drawback of the device, however, is the awkward manner in which it must be used. To view the graduated dosage indicia on the syringe barrel, the device, syringe and vial must be hand held together during loading of the syringe.

Consequently, none of the above inventions and patents, taken either singly or in combination, is seen to describe the instant invention as claimed. Thus, an insulin syringe with magnified sheath solving the aforementioned problems is desired.

SUMMARY OF THE INVENTION

The insulin syringe with magnified sheath is a syringe with a transparent outer sleeve constructed of a material capable of magnifying printed information. The outer sleeve is slidably attached to the syringe barrel and locks into a retracted position where it surrounds the syringe barrel and magnifies the dosage indicia thereon while exposing the syringe needle for use, or locks into an extended position where it surrounds the needle to help prevent inadvertent needle sticks. Because the sheath is permanently attached and slides easily between its two extreme positions, the invention requires minimal finger dexterity for proper use.

Accordingly, it is a principal object of the invention to provide an insulin syringe with an outer sleeve that functions both to magnify dosage indicia on the syringe barrel and to protect against inadvertent needle sticks.

It is another object of the invention to provide an insulin syringe with an outer sleeve that can lock into a retracted position where it magnifies the dosage indicia on the syringe barrel and exposes the needle for use.

It is a further object of the invention to provide an insulin syringe with an outer cover that can lock into an extended position where it surrounds the syringe needle and thereby prevents inadvertent needle sticks.

Still another object of the invention is to provide an insulin syringe with an outer sleeve where the outer sleeve consists of a single part.

Yet another object of the invention is to provide an insulin syringe with an outer sleeve where the outer sleeve does not require an adapter to function with that syringe.

Furthermore, it is an object of the invention to provide an insulin syringe with an outer cover that requires a minimal level of finger dexterity for proper use.

Moreover, it is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
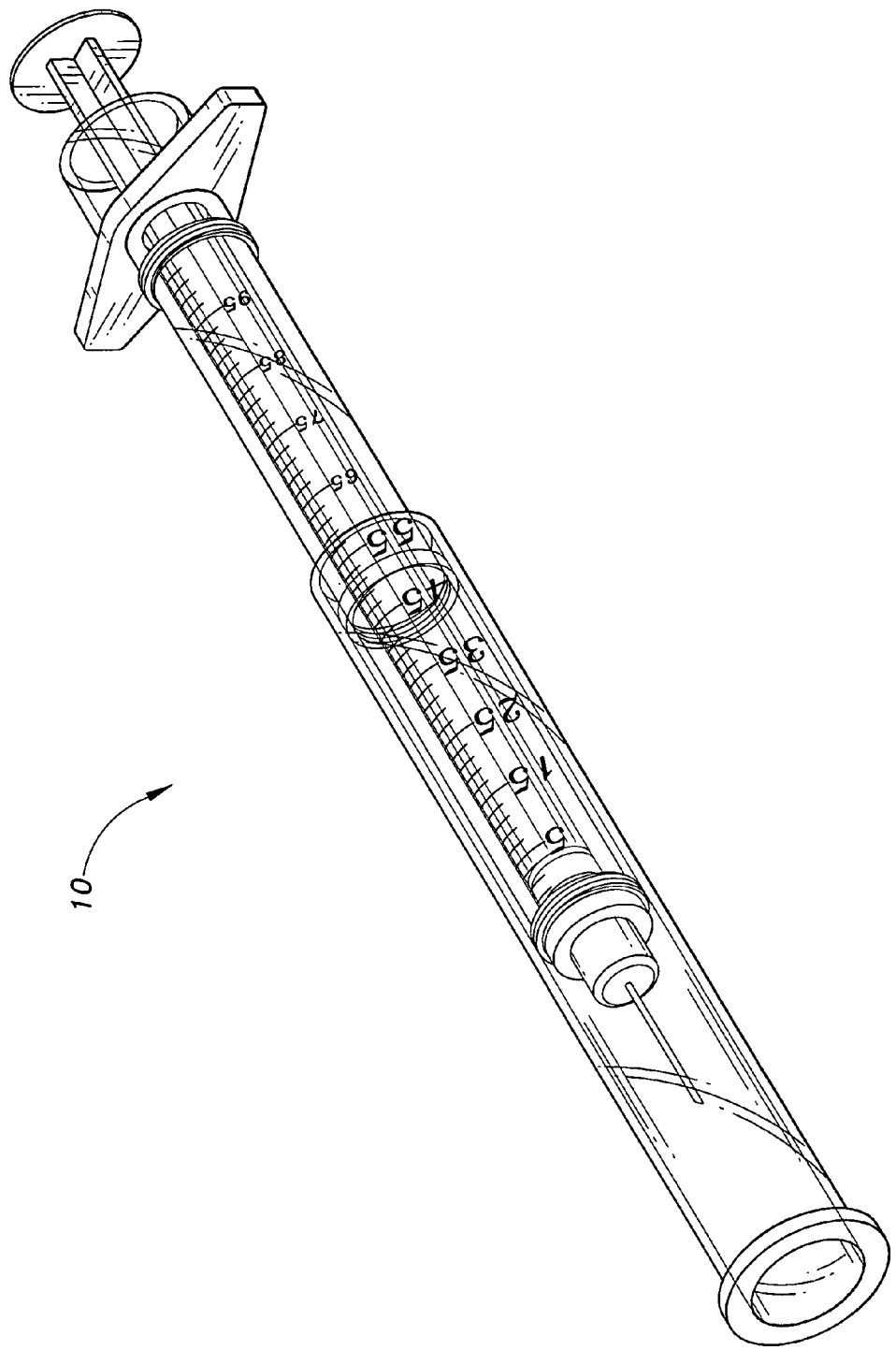
FIG. 1 is a perspective view of an insulin syringe with magnified sheath according to the present invention.
Figure 2:
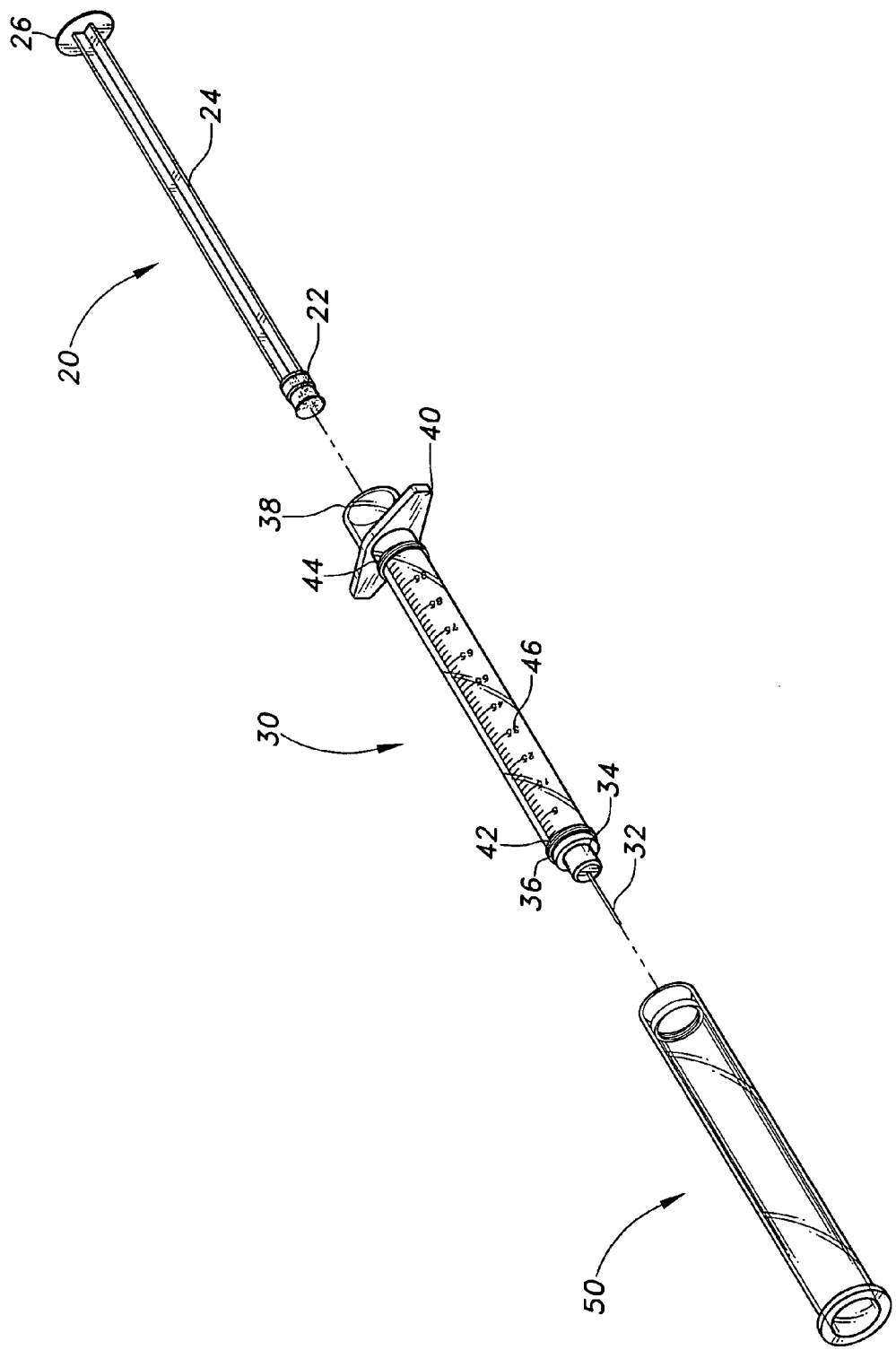
FIG. 2 is an exploded view of FIG. 1.

The present invention is an insulin syringe with magnified sheath, designated generally as 10 in the drawings, that is designed to provide diabetics an added measure of safety when loading a syringe with insulin for self-injection. As shown in FIG. 2, the invention 10 includes a syringe barrel 30, a syringe plunger 20, and a sheath 50.

The syringe barrel 30 and syringe plunger 20 are similar to those of a conventional syringe with the exception that the barrel 30 is threaded in two places 42 and 44. The barrel 30 is cylindrical, hollow and substantially clear with a needle 32 attached to its 30 distal end 36 end via a needle bracket 34. The proximal end 38 of the barrel 30 is open and adapted for receiving the plunger 20 plug 22. The outer circumference of the barrel 10 is threaded 42 and 44 near both its distal and proximal ends 36 and 38. A finger grip 40 extends laterally from two sides of the barrel 30 in a plane that is orthogonal to the axis of the barrel 30. Graduated dosage indicia 46 are printed along the side of the barrel 30.

The plunger 20 consists of an elongated stem 24 with a plug 22 attached at one end and a thumb push 26 formed at the other end. When the plunger 20 is inserted into the barrel 30, the outer circumference of the plug 22 forms an air-tight seal with the inner wall of the barrel 30 which enables the syringe 10 to hold a liquid medication such as insulin.

Figure 3:
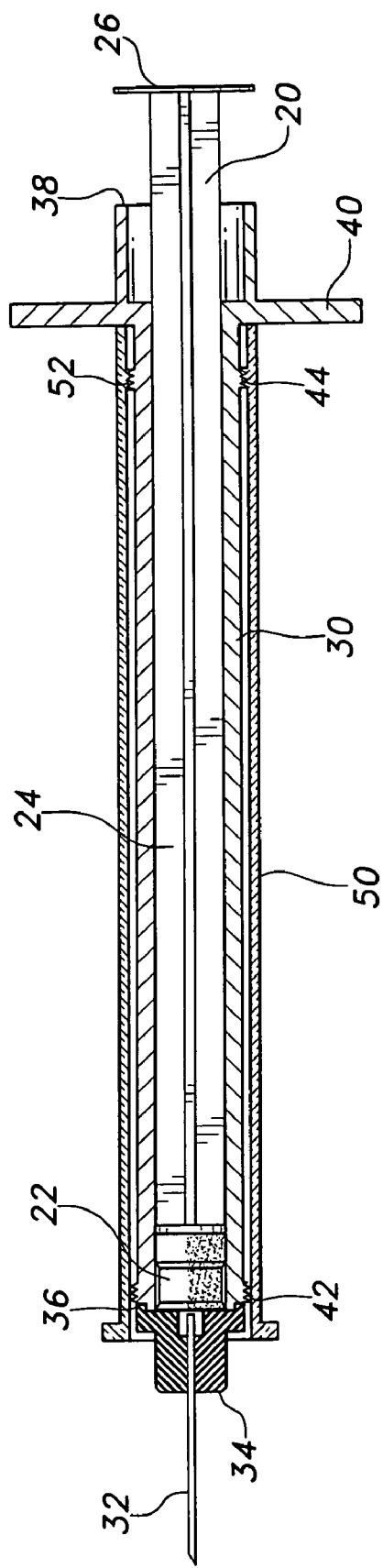
FIG. 3 is a partially fragmented view of an insulin syringe with magnified sheath according to the present invention with the sheath and syringe barrel shown in cross section.
Figure 4:
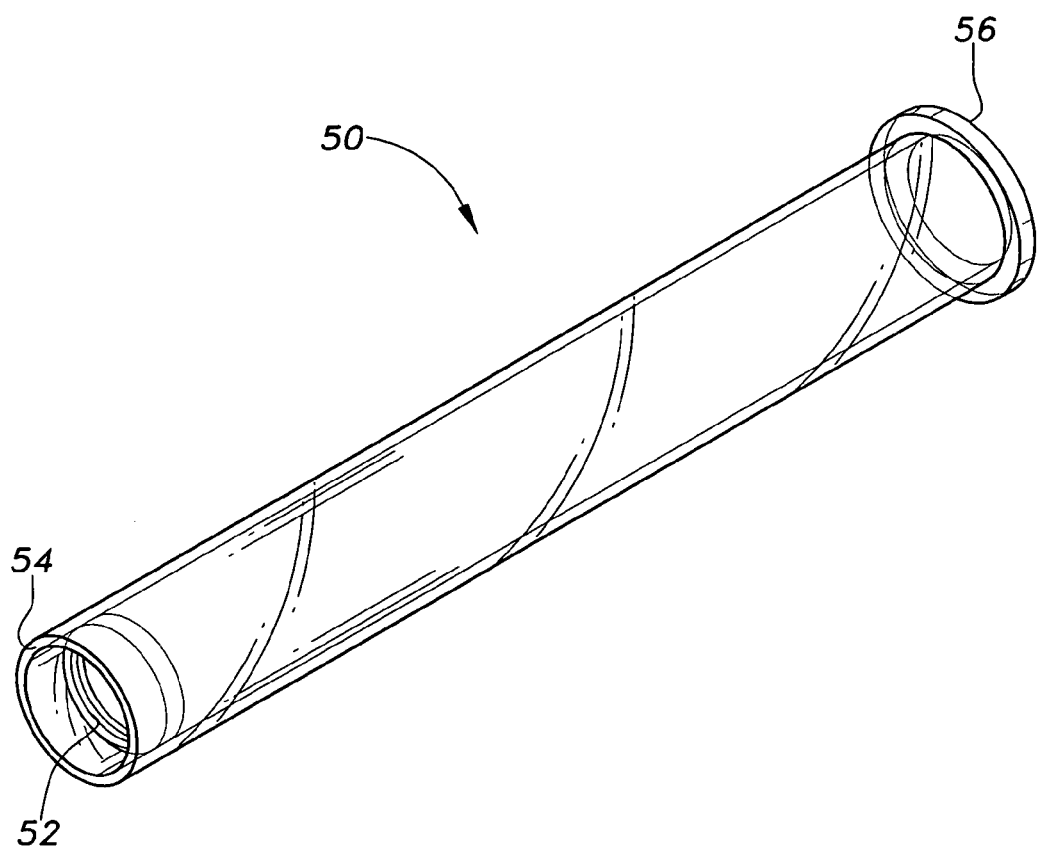
FIG. 4 is a perspective view of a sheath for an insulin syringe with magnified sheath according to the present invention.

The sheath 50 is cylindrical, hollow, transparent and constructed of a magnifying material such as Lucite ☙. It 50 is threaded 52 internally near its 50 proximal end 54 and is slidably coupled with the syringe barrel 30 in a manner that allows for axial rotation around the barrel 30 and longitudinal movement between two positions relative to the barrel 30. In the retracted position, the sheath 50 is positioned over the barrel 30 with the needle 32 exposed for use and with the proximal end 54 of the sheath 50 near the proximal end 38 of the barrel 30, as depicted in FIG. 3. By rotating the sheath 50 clockwise in this position, the sheath 50 threading 52 interlocks with the barrel threading 44 located near the proximal end 38 of the barrel 30 and thereby locks the sheath 50 into this position. In this position, the sheath 50 completely covers and magnifies the graduated dosage indicia 46 on the barrel 30.

In the extended position, the sheath 50 is positioned around the needle 32 to prevent inadvertent needle sticks. Its 50 proximal end 54 is positioned near the distal end 36 of the barrel 30 and, when the sheath is axially rotated counter clockwise, its 50 threading 52 interlocks with the barrel threading 42 at the distal end 36 of the barrel 30 and thereby locks the sheath 50 in this position.

It is to be understood that the present invention is not limited to the embodiment described above, but encompasses any and all embodiments within the scope of the following claims.

I claim:

1. An insulin syringe with magnified sheath, comprising:
   a syringe including a needle, a barrel and a plunger with said barrel having dosage indicia thereon; and
   a sheath being cylindrical, constructed of a transparent, magnifying material, and dimensioned to surround said barrel of said syringe;
   said sheath being slidably coupled with said barrel of said syringe;
   said sheath being constructed for axial rotation around said barrel; and
   said sheath being constructed for longitudinal movement between a retracted position in which said sheath is disposed over said barrel with said needle exposed for use, and an extended position in which said sheath surrounds said needle thereby preventing inadvertent needle sticks;
   wherein, when in its retracted position, said sheath magnifies said dosage indicia on said barrel of said syringe regardless of rotational position of said sheath relative to said barrel.

2. The insulin syringe with magnified sheath according to claim 1, wherein:
   each of said sheath and said barrel has a proximal end and a distal end;
   said barrel being threaded around a portion of its outer circumference near each of said distal and said proximal ends; and
   said sheath being threaded around a portion of its inner circumference near said proximal end;
   wherein, when said sheath is in said retracted position, clockwise axial rotation of said sheath engages threading of said sheath with threading near proximal end of said barrel; and
   wherein, when said sheath is in said extended position, counter-clockwise axial rotation of said sheath engages threading of said sheath with threading near distal end of said barrel;
   whereby, said sheath is locked in either of said retracted or said extended positions by engaging threading of said sheath with threading of, respectively, either said proximal end or said distal end of said barrel.

3. The insulin syringe with magnified sheath according to claim 1, wherein:
   said sheath is constructed of methyl methacrylate.

* * * * *